US012168387B2

(12) United States Patent
Deliwala

(10) Patent No.: US 12,168,387 B2
(45) Date of Patent: Dec. 17, 2024

(54) ADAPTIVE ENVIRONMENTAL CONTROLS IN A VEHICLE

(71) Applicant: Analog Devices, Inc., Norwood, MA (US)

(72) Inventor: Shrenik Deliwala, Andover, MA (US)

(73) Assignee: ANALOG DEVICES, INC., Norwood, MA (US)

( * ) Notice: Subject to any disclaimer, the term of this patent is extended or adjusted under 35 U.S.C. 154(b) by 492 days.

(21) Appl. No.: 16/826,258

(22) Filed: Mar. 22, 2020

(65) Prior Publication Data

US 2020/0346518 A1    Nov. 5, 2020

Related U.S. Application Data

(60) Provisional application No. 62/840,996, filed on Apr. 30, 2019.

(51) Int. Cl.
*B60H 1/00* (2006.01)
*A61B 5/00* (2006.01)
*A61B 5/01* (2006.01)
*A61B 5/083* (2006.01)

(52) U.S. Cl.
CPC ........... *B60H 1/00742* (2013.01); *A61B 5/01* (2013.01); *A61B 5/0836* (2013.01); *A61B 5/6893* (2013.01); *B60H 1/00785* (2013.01); *B60H 1/00835* (2013.01); *B60H 1/008* (2013.01)

(58) Field of Classification Search
CPC .............. B60H 1/0073; B60H 1/00735; B60H 1/00742; B60H 1/00771; B60H 1/00785; B60H 1/008; B60H 1/00821; B60H 1/00835
See application file for complete search history.

(56) References Cited

U.S. PATENT DOCUMENTS

| 2002/0145516 A1* | 10/2002 | Moskowitz ............ B60H 1/008 340/541 |
| 2002/0189332 A1 | 12/2002 | Schell |
| 2009/0146813 A1 | 6/2009 | Nuno |

(Continued)

OTHER PUBLICATIONS

ANSI/ASHRAE Addendum p to ANSI/ASHRAE Standard 62.I-2013; "Ventilation for Acceptable Indoor Air Quality", 2015, ISSN 11041-2336.

(Continued)

*Primary Examiner* — Frantz F Jules
*Assistant Examiner* — Jason N Thompson
(74) *Attorney, Agent, or Firm* — ArentFox Schiff LLP

(57) ABSTRACT

System and apparatus for carbon dioxide detection within an automobile. Specifically, this disclosure describes apparatuses and systems for optical gas detection in a stationary and moving vehicle. There is a need for a such a system to prevent loss of life and contribute to a safer traffic environment. This disclosure provides a highly efficient optical measurement system based on principals of optical absorption spectroscopy. It detects the presence of neglected children and animals and changes the vehicle's interior environment accordingly so as to preclude many potentially dangerous conditions. The present disclosure can also optimize ventilation for a driver. To this end, a driver can maximize alertness and attentiveness.

17 Claims, 10 Drawing Sheets

(56) References Cited

U.S. PATENT DOCUMENTS

| | | | |
|---|---|---|---|
| 2012/0015594 A1* | 1/2012 | Yenneti | B60H 1/00849 |
| | | | 454/75 |
| 2013/0324024 A1* | 12/2013 | Remmers | B60H 1/00964 |
| | | | 454/75 |
| 2015/0118946 A1 | 4/2015 | Yeon | |
| 2016/0052363 A1* | 2/2016 | Ostermeier | B60H 1/00985 |
| | | | 165/250 |
| 2016/0103111 A1* | 4/2016 | Griffin | B60N 2/002 |
| | | | 73/25.01 |
| 2016/0167479 A1* | 6/2016 | Morin | B60H 1/00742 |
| | | | 701/48 |
| 2018/0194194 A1* | 7/2018 | Lyubich | B60H 1/00742 |
| 2020/0062080 A1* | 2/2020 | Hernandez | B60H 1/00978 |

OTHER PUBLICATIONS

Taku OSHIMA et al., "Can calculation of energy expenditure based on CO2 measurements replace indirect calorimetry?"; Critical Care (2017) 21:13.

J. B. De V. Weir, "New Methods for Calculating Metabolic Rate with Special Reference to Protein Metabolism", J. Physiol., (1949) 109, 1-9.

* cited by examiner

ADAPTIVE ENVIRONMENTAL CONTROLS IN A VEHICLE

CROSS-REFERENCE TO RELATED APPLICATIONS

This application is related to and claims the benefit of priority under 35 U.S.C. § 119(e) to U.S. Provisional Patent Application No. 62/840,996 entitled, "ADAPTIVE ENVIRONMENTAL CONTROLS IN A VEHICLE" filed on Apr. 30, 2019 related to U.S. patent application Ser. No. 15/993,188 entitled, "COMPACT OPTICAL GAS DETECTION SYSTEM AND APPARATUS" filed on May 30, 2018, and U.S. patent application Ser. No. 16/699,677 entitled, "FIRE DETECTION SYSTEM" filed on Dec. 1, 2019, all of which are hereby incorporated by reference in their entirety.

FIELD OF THE DISCLOSURE

The present disclosure relates to mammal presence detection in a vehicle. More specifically, this disclosure describes apparatuses and systems for people and animal detection in an automobile using measured carbon dioxide in a ventilation circulatory system.

BACKGROUND

Carbon Dioxide can be used to estimate whether an infant or a small animal is left in the car with all the windows closed. Such negligence leads to large numbers of unnecessary infant deaths. It can also be used to automatically control the ventilation system in a moving car to best manage the heating and cooling system as well as keep the level of $CO_2$ within reasonable limits. Recent findings suggest that drowsiness may be induced by high $CO_2$ levels.

The main components of an $CO_2$ vehicle sensor are an infrared source (lamp), a sample chamber or light tube, a light filter and an infrared detector. The IR light is directed through the sample chamber towards the detector. In parallel, there is another chamber with an enclosed reference gas, typically nitrogen. The gas in the sample chamber causes absorption of specific wavelengths according to the Beer-Lambert law, and the attenuation of these wavelengths is measured by the detector to determine the gas concentration. The detector has an optical filter in front of it that eliminates all light except the wavelength that the selected gas molecules can absorb.

Ideally other gas molecules do not absorb light at this wavelength, and do not affect the amount of light reaching the detector however some cross-sensitivity is inevitable. For instance, many measurements in the IR area are cross sensitive to $H_2O$ so gases like $CO_2$, $SO_2$ and $NO_2$ often initiate cross sensitivity in low concentrations.

A common application is to use a NDIR (non-dispersive infrared absorbance) sensor to monitor $CO_2$. Most molecules can absorb infrared light, causing them to bend, stretch or twist. The amount of IR light absorbed is proportional to the concentration. The energy of the photons is not enough to cause ionization, and thus the detection principle is very different from that of a photoionization detector (PID). Ultimately, the energy is converted to kinetic energy, causing the molecules to speed up and thus heat the gas. A familiar IR light source is an incandescent household bulb. Each molecule absorbs infrared light at wavelengths representative of the types of bonds present.

Many techniques have been proposed which typically consist of a broadband light source. Unfortunately, they require relatively long optical paths which reduce light collection efficiencies. The inventor of the present disclosure has identified these shortcomings and recognized a need for a more elegant, robust, compact optical gas detection measurement system with high collection efficiency. That is, the inventor has come up with a compact, low-power, optical gas detection apparatus which can be mass produced via packaging without yielding accuracy.

Accordingly, there is a need for $CO_2$ gas detection in conjunction with infant and mammal detection, particularly in transportation vehicles. The inventors of the present disclosure have identified these shortcomings and recognized a need for a new safety equipment which is easily implemented into manufacturing assemblies.

This overview is intended to provide an overview of subject matter of the present patent application. It is not intended to provide an exclusive or exhaustive explanation of the invention. Further limitations and disadvantages of conventional and traditional approaches will become apparent to one of skill in the art, through comparison of such systems with some aspects of the present invention as set forth in the remainder of the present application with reference to the drawings.

SUMMARY OF THE DISCLOSURE

System and apparatus for carbon dioxide detection within an automobile. Specifically, this disclosure describes apparatuses and systems for optical gas detection in a stationary and moving vehicle. There is a need for a such a system to prevent loss of life and contribute to a safer traffic environment. This disclosure provides a highly efficient optical measurement system based on principals of optical absorption spectroscopy. It detects the presence of neglected children and animals and changes the vehicle's interior environment accordingly so as to preclude many potentially dangerous conditions. The present disclosure can also optimize ventilation for a driver. To this end, a driver can maximize alertness and attentiveness.

According to one aspect of the present disclosure, an opto-electronic package for measuring $CO_2$ and temperature sensor placed in the ventilation system or in the cabin of the automobile to measure the total concentration of the gas when a car is parked to ascertain the presence of the living human or pet and its metabolic rate is disclosed.

According to another aspect of the present disclosure, this is done by intermittently and automatically running the ventilation system to sample the air in the cabin.

According to another aspect of the present disclosure, the automobile can send a distress call to emergency services or a responsible party based on the calculated heat stress.

According to another aspect of the present disclosure, one or more sensors are used to estimate the number of people/animals in the car.

According to another aspect of the present disclosure, this sensor includes temperature detection.

According to another aspect of the present disclosure, this sensor includes $CO_2$ detection.

According to another aspect of the present disclosure, the sensing comprises $CO_2$ detection and temperature detection.

According to another aspect of the present disclosure, detection methods are combined with weight information from the seat to improve the estimate of the type and number of people in the car.

According to another aspect of the present disclosure, the estimate of the number of people in the car is improved by deliberating changing the Air Exchange Rate (AER) of the car by modulating the ventilation system.

According to another aspect of the present disclosure, this sensor includes CO2 detection in conjunction with a particulate measuring unit to optimize cabin air quality.

According to one aspect of the present disclosure, an opto-electronic package for measurement of absorption of light comprises a cap covering the substrate to form a cavity for measurement of absorption of gas.

According to another aspect of the present disclosure, the opto-electronic package for measurement of absorption of light further comprises a substrate with a light source disposed on it.

According to another aspect of the present disclosure, the opto-electronic package for measurement of absorption of light further comprises a substrate with at least one detector to which the cap is attached.

According to another aspect of the present disclosure, the inner shape of the cap forms a mirror in which the mirror shape is derived from the two elliptical mirror surfaces inclined substantially at 45 degrees to provide high collection of the light source to the detector.

According to another aspect of the present disclosure, the cap provides for openings for the diffusion of gas molecules.

According to another aspect of the present disclosure, the substrate and the cap provide a method of alignment to each other.

According to another aspect of the present disclosure, the opto-electronic package for measurement of absorption of light further comprises a substrate with at least two detectors disposed thereon.

According to another aspect of the present disclosure, wherein the first detector acts as a reference detector that is measures light such that its signal is substantially insensitive to the absorption by a predetermined gas.

According to another aspect of the present disclosure, the second detector that may have either an optical filter attached to it or provided on top of it to make it substantially sensitive to the absorption by the predetermined gas.

According to another aspect of the present disclosure, the opto-electronic package for measurement of absorption of light further comprises many detectors in which at least one detector acts as a reference detector and the other detectors' optical filters have applied to them so as to detect different gases present in the cavity.

According to another aspect of the present disclosure, the light source may be an LED or a thermal light source.

According to another aspect of the present disclosure, the opto-electronic package for measurement of absorption of light further comprises a substrate with a light source disposed on it. LED may have a center wavelength from 0.2-12 μm.

According to another aspect of the present disclosure, the detector may use direct photon absorption or may use an indirect method of measurement that includes conversion to heat to measure light flux.

According to another aspect of the present disclosure, direct photon detectors include detectors made from PbSe, PbS, HgCdTe, GaSb/InAs superlattice etc.

According to another aspect of the present disclosure, indirect thermal detectors include pyroelectrics, bolometers, etc.

According to another aspect of the present disclosure, the predetermined gas may be CO2, water vapor, methane, NO, as well as vapors of various alcohols.

According to another aspect of the present disclosure, the predetermined gas may be any of the gases used in anesthesia.

According to another aspect of the present disclosure, the predetermined gas may be vapors of diesel, kerosene, or gasoline.

According to another aspect of the present disclosure, multiple gases may be simultaneously detected by using multiple detectors with optical filters chosen for each of the gases and using a broadband light source.

According to another aspect of the present disclosure, the predetermined gases may be CO2 and alcohol vapor which are simultaneously detected for breadth analysis.

According to another aspect of the present disclosure, the predetermined gases may be water and alcohol vapor which are simultaneously detected for breadth analysis.

According to another aspect of the present disclosure, the opto-electronic package for measurement of absorption of light further comprises that the openings to the cavity that forms the cap may be covered with fine mesh to prevent larger dust particles from entering the cavity.

According to another aspect of the present disclosure, the opto-electronic package for measurement of absorption of light further comprises that the package is constructed with "base package" that can be tested separately from the gas chamber and the two combined by assembly to form the complete gas detection system.

The drawings show exemplary vehicle sensors and configurations. Variations of these circuits, for example, changing the positions of, adding, or removing certain elements from the circuits are not beyond the scope of the present invention. The illustrated smoke detectors, configurations, and complementary devices are intended to be complementary to the support found in the detailed description.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

For a fuller understanding of the nature and advantages of the present invention, reference is made to the following detailed description of preferred embodiments and in connection with the accompanying drawings, in which.

DETAILED DESCRIPTION

The present disclosure relates to mammal presence detection in a vehicle. More specifically, this disclosure describes apparatuses and systems for people and animal detection in an automobile using measured carbon dioxide in a ventilation circulatory system. In one or more embodiments, a vehicle can adaptively change the internal environment based on measured inputs. For example, a vehicle could lower windows and/or turn on air conditioning if it detects the presence of a person or animal in a hot stationary car.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

Figure 1:
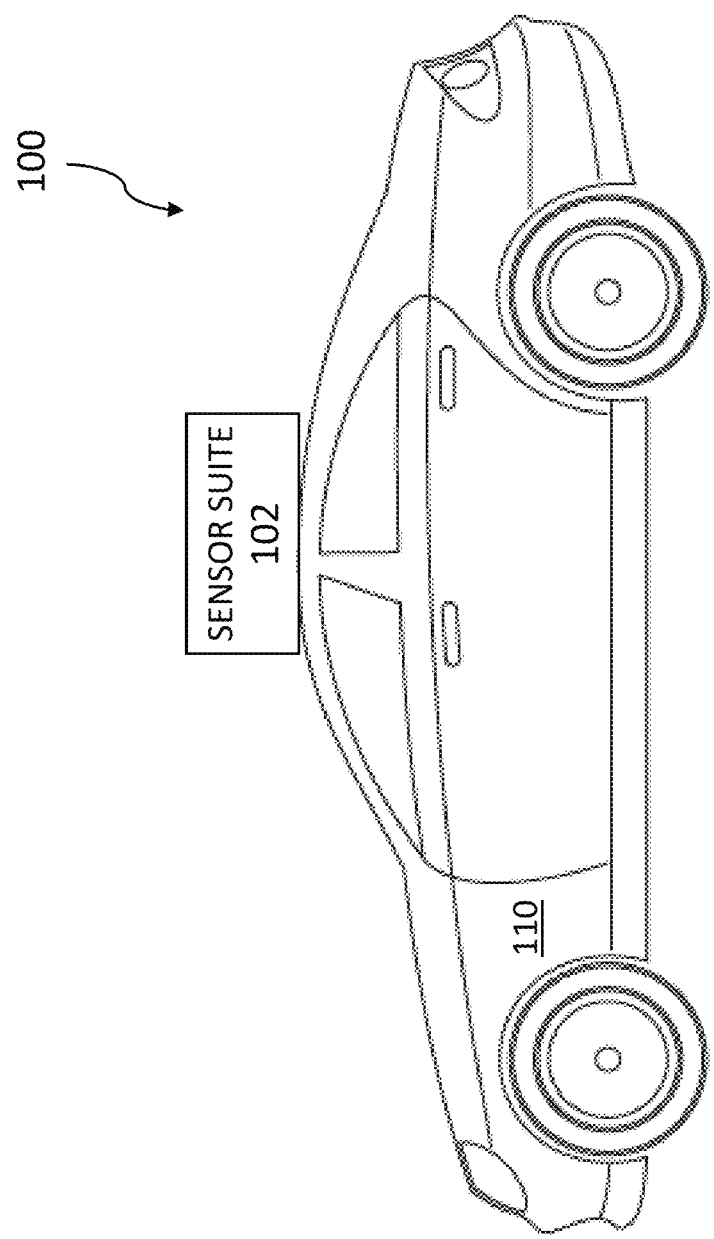
FIG. 1 shows an exemplary side view of an automobile sensory system, in accordance with one or more embodiments of the disclosure provided herein.

FIG. 1 shows an exemplary side view of an automobile sensor system 100, in accordance with one or more embodiments of the disclosure provided herein. In one or more embodiments, automobile sensor system 100 comprises car 110 and sensor suite 102. Sensor suite 102 comprises one or more of gas sensor, $CO_2$ sensor, particulate matter sensor, temperature sensor, humidity sensor, and/or GPS device.

In some embodiments, carbon dioxide is monitored and the recirculation is adjusted accordingly in that, when $CO_2$ levels are too high, the vehicle lets in more fresh air. A key object in achieving this is a quick (low latency) gas monitor. The standard in the art takes several minutes. The present disclosure and incorporated references are orders of magnitudes faster.

A gas detector is a device that detects the presence of gases in an area, often as part of a safety system. This type of equipment is used to detect a gas leak or other emissions and can interface with a control or safety systems so a process can be automatically shut down or other action which will be discussed later. A gas detector can sound an alarm to occupants where a leak is occurring, giving them the opportunity to leave. This type of device is important because there are many gases that can be harmful to organic life, such as humans or animals.

In other embodiments, particulate matter is measured and monitored. Even the most robust filtration systems cannot remove this during a single circulation, e.g., 60% removal rate would be optimistic. As such, the vehicle could choose to let in less fresh air in order to filter a greater percentage of particulate matter—which tends to be more deleterious than higher $CO_2$. Of course, this is an engineering tradeoff.

Particulates—also known as atmospheric aerosol particles, atmospheric particulate matter, particulate matter (PM), or suspended particulate matter (SPM)—are microscopic particles of solid or liquid matter suspended in the air. The term aerosol commonly refers to the particulate/air mixture, as opposed to the particulate matter alone.

In a similar embodiment, sensor suite 102 can comprise an air pollution sensor. Air pollution sensors are devices that monitor the presence of air pollution in the surrounding area. They can be used for both indoor and outdoor environments. These sensors are typically built at home or bought from certain manufacturers. Although there are various types of air pollution sensors, and some are specialized in certain aspects, the majority focus on five components: ozone, particulate matter, carbon monoxide, sulfur dioxide, and nitrous oxide.

In still other embodiments, the present disclosure can monitor any gas and/or water vapor, such as a humidity sensor. A hygrometer is an instrument used to measure the amount of humidity and water vapor in the atmosphere, in soil, or in confined spaces. Humidity measurement instruments usually rely on measurements of some other quantity such as temperature, pressure, mass, a mechanical or electrical change in a substance as moisture is absorbed. By calibration and calculation, these measured quantities can lead to a measurement of humidity.

In other embodiments, dew point could be calculated using a temperature sensor. In some embodiments, a thermistor is used as a temperature sensor. However, other suitable temperature sensors, such as mechanical, electrical (thermocouple, resistance thermometer, and Silicon bandgap), and integrated sensor circuits are not beyond the scope of the present invention.

In yet further embodiments, GPS tracking could aid in the tracking and particulate matter determination. For example, in some cities with known pollution, the vehicle would choose a higher recirculation rate. Additionally, the same change could be made if fires are reported in the area.

A Satellite navigation device, colloquially called a GPS receiver, or simply a GPS, is a device that is capable of receiving information from global navigation satellite system satellites and then to calculate the device's geographical position. Using suitable software, the device may display the position on a map, and it may offer routing directions. The Global Positioning System (GPS) is one of a handful of global navigation satellite systems (GNSS). Other navigation systems are not beyond the scope of the present invention.

One of the most popular techniques for quantitative measurement of the industrially significant gases such as $CO_2$, $NO_x$, water vapor, methane etc. is carried out by optical absorption. Most of these gases have strong vibrational absorption spectra in the 1-12 μm region of electromagnetic spectrum and include various vibrational modes and its overtones.

A fundamental measurement technique consists of measuring changes in the extinction of the light source at a particular wavelength of interest as the concentration of the target gas is varied. This technique is popularly called non-dispersive infra-red (NDIR) technique.

There are no devices available on the market which provide for automobile detection of passenger's life-threatening capacity. However, these typically could include a broadband light source—thermal such as light bulb or a compact heater or an LED—whose output is passed through an optical system that provides a relatively long path length for absorption of gas and a detector system to measure extinction. Small holes in the optical system allows the gas to diffuse into the light path.

The detector system itself may consist of two detectors. One detector provides a reference signal and is specifically tuned to reduce or avoid gas absorption lines of interest to measure drift and changes in the light source and condition of the optical channel. The other detector is tuned to the wavelength of absorption of the gas to be measured.

Many configurations of the optical systems have been proposed in the past, and some of these devices are available on the market. Yet, none of which attempt to address the present need which the inventor of the present disclosure has acutely recognized.

Figure 2:
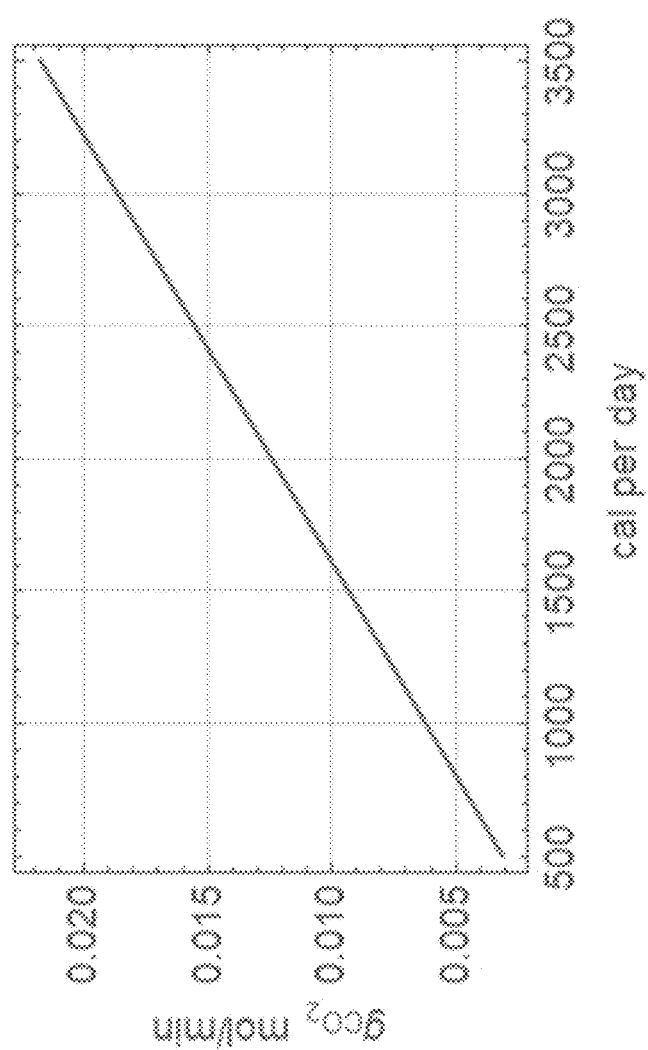
FIG. 2 demonstrates an exemplary graph of indirect calorimetry as a function of glucose, in accordance with some embodiments of the disclosure provided herein.

FIG. 2 demonstrates an exemplary graph of indirect calorimetry as a function of glucose, in accordance with some embodiments of the disclosure provided herein.

One of the most popular gases to be measured is $CO_2$. In the discussion below on the design of a novel optical package, the focus will be on $CO_2$ gas to make the discussion specific, but the principal applies to many of the industrially relevant gases mentioned earlier and is quite general.

First non-limiting premise: the $CO_2$ produced by humans and other animals in the air in the car's passenger cabin can be measured.

Another non-limiting premise: the instantaneous concentration of $CO_2$ in well-mixed air in the cabin depends on the air exchange rate (AER) and the total $CO_2$ produced.

Another non-limiting premise: a relatively sensitive time-dependent measurement by placing a $CO_2$ sensor in the ventilation system of the car can be used to estimate the level of pollutants, air-freshness, and number of passengers in a still or moving car.

If the cabin has volume $V_0$ and the rate of generation of $CO_2$ in the cabin is denoted by $g_{co_2}$ and if we further assume that the $CO_2$ is rapidly mixed uniformly within the cabin volume (or mixed by the ventilation system) then the concentration of the $CO_2$ may be written as:

$$V_0 \left( \frac{dc(t)}{dt} \right) = (c_{in} - c(t))AERV_0 + g_{co_2} V_{STP} \quad (1)$$

Note that each term in the equation simply measures the rate of change of the molecular density of $CO_2$ molecules. $V_{STP}$ is 22.4 liters/mol at STP and $g_{co_2}$ is the generation rate in moles. The solution to the above equation gives:

$$c(t) = \left(c_0 e^{-ACMt} + c_{in}(1 - e^{-ACMt})\right) + \left(\frac{g_{co_2} V_{STP}}{ACMV_0}\right)(1 - e^{-ACMt}) \quad (2)$$

In the equation above, time is measured in minutes, ACM air changes per minute which is also frequently expressed as Air Exchange Rate (AER) in the units of air exchanges per minute, $c_0$ is the initial value of the concentration, and $c_{in}$ is the concentration in the fresh air being exchanged.

As is known in the art, air changes per hour, abbreviated ACPH or ACH, or air change rate is a measure of the air volume added to or removed from a space (normally a room or house) divided by the volume of the space. If the air in the space is either uniform or perfectly mixed, air changes per hour is a measure of how many times the air within a defined space is replaced.

Typical starting point for $c_0 = c_{in} \sim 400$ ppm but the solution of the Equation 1 can be applied to any general condition. The generation of $CO_2$ is driven by the metabolic rate.

Weir's formula is often used to estimate the caloric consumption from the measured $CO_2$. There are many instances of this use in the clinical practice. The inventor of the present disclosure and authors of other journal articles have found good correlation of the Weir formula.

But without losing generality and in order to illustrate the point we will assume respiration quotient RQ~1 and use the fact that enthalpy of combustion of glucose is 2.8 MJ/mol. Using this assumption, one gets the rate of generation of $CO_2$ in mol/min as:

$$g_{CO_2} \sim cal_{min} * 6 \frac{4.18}{2800} \quad (3)$$
$$\sim \frac{cal_{day}}{1440} * 6 \frac{4.18}{2800}$$
$$= 6.2 \; 10^{-6} \; cal_{day}$$

The relationship in Equation (3) is plotted in FIG. 2 and is adequate for illustrating the principle of this disclosure. Weir's formula and other similar estimates of total energy expenditure or TEE can be used to more accurately generate expected $CO_2$ generation rate. A more practical rate that is often used by vehicle manufacturers and ASHRAE is measured in ppm/h and is $S_{co_2} = g_{co_2} V_{STP}$. Accordingly, FIG. 2 can be replotted which is depicted in FIG. 3.

Figure 3:
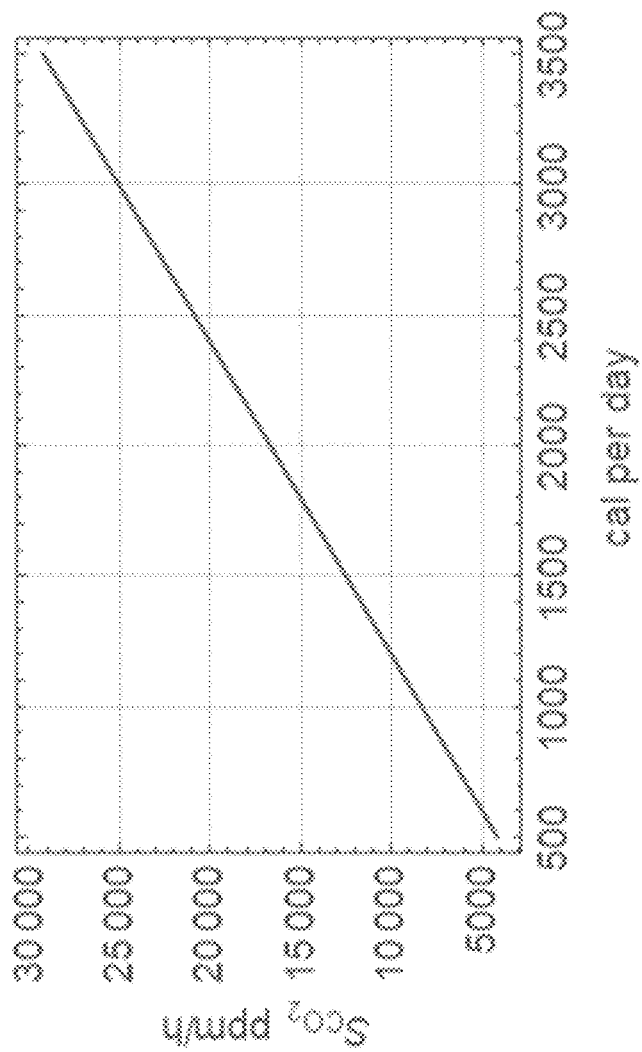
FIG. 3 demonstrates an exemplary graph of indirect calorimetry as a function of glucose and gas volume, in accordance with some embodiments of the disclosure provided herein.
Figure 4:
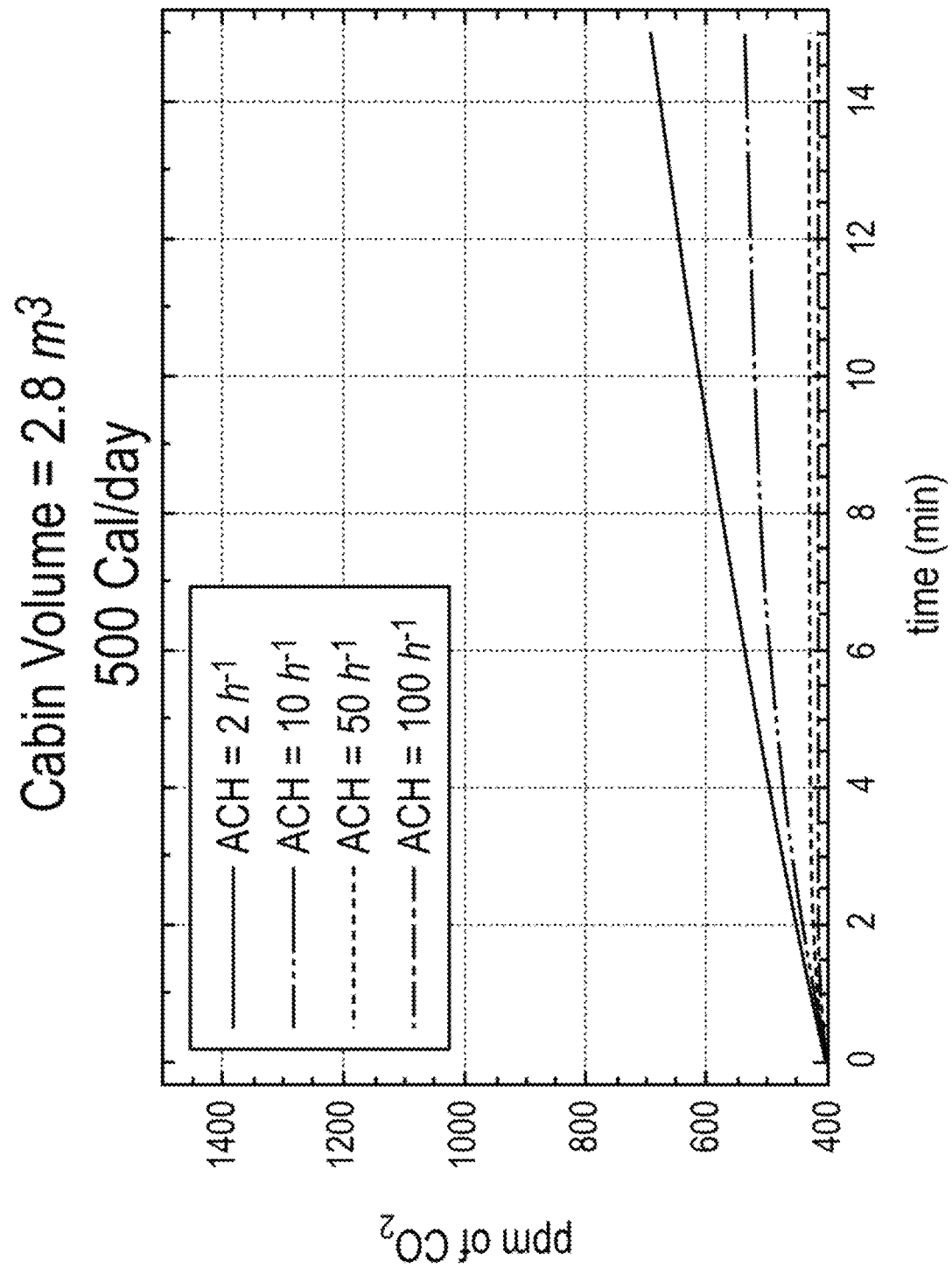
FIG. 4 demonstrates an exemplary graph of indirect calorimetry as a predetermined daily caloric intake for different air exchange rates, in accordance with some embodiments of the disclosure provided herein.
Figure 5:
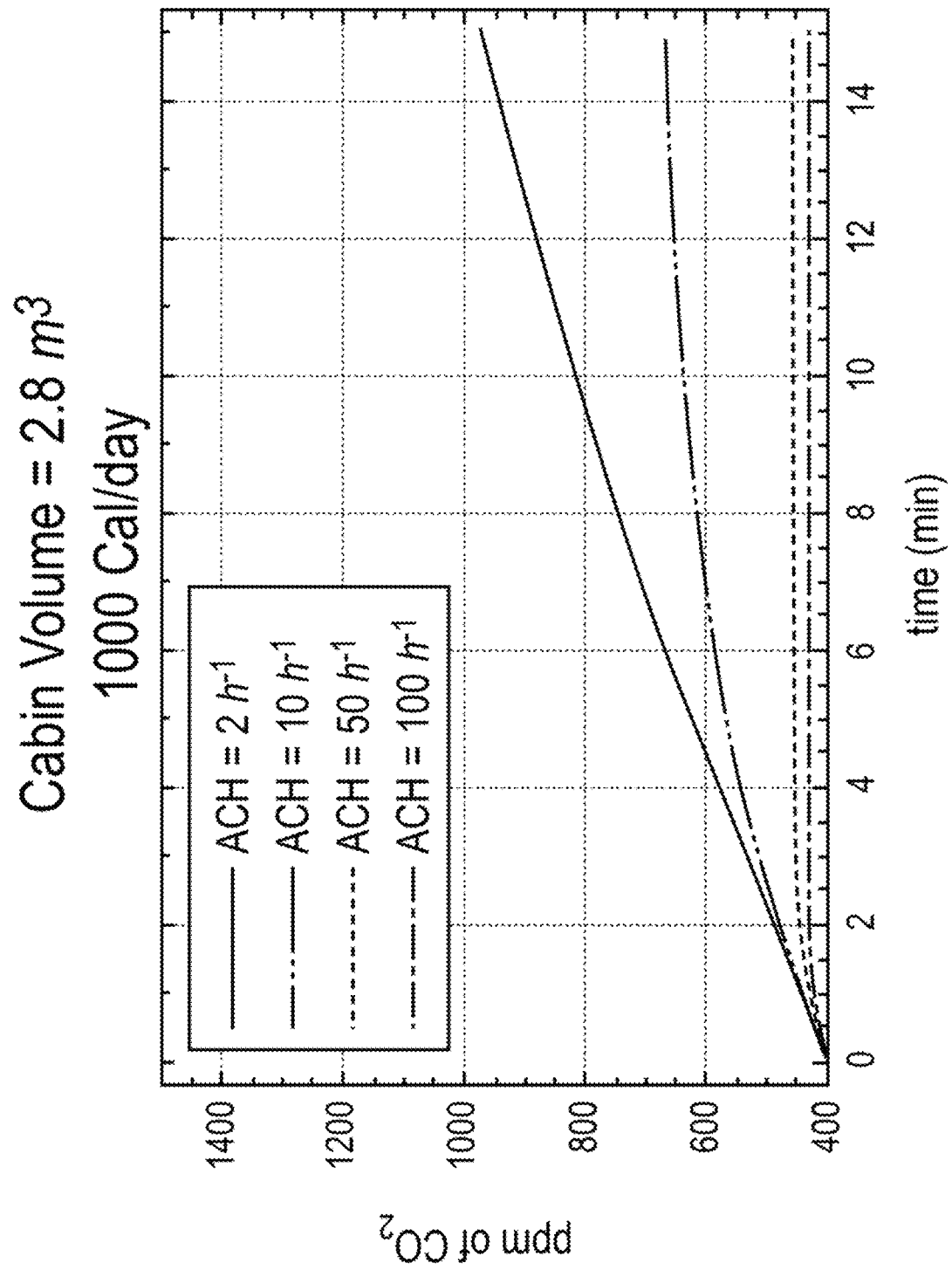
FIG. 5 demonstrates an exemplary graph of indirect calorimetry as a predetermined daily caloric intake for different air exchange rates, in accordance with some embodiments of the disclosure provided herein.
Figure 6:
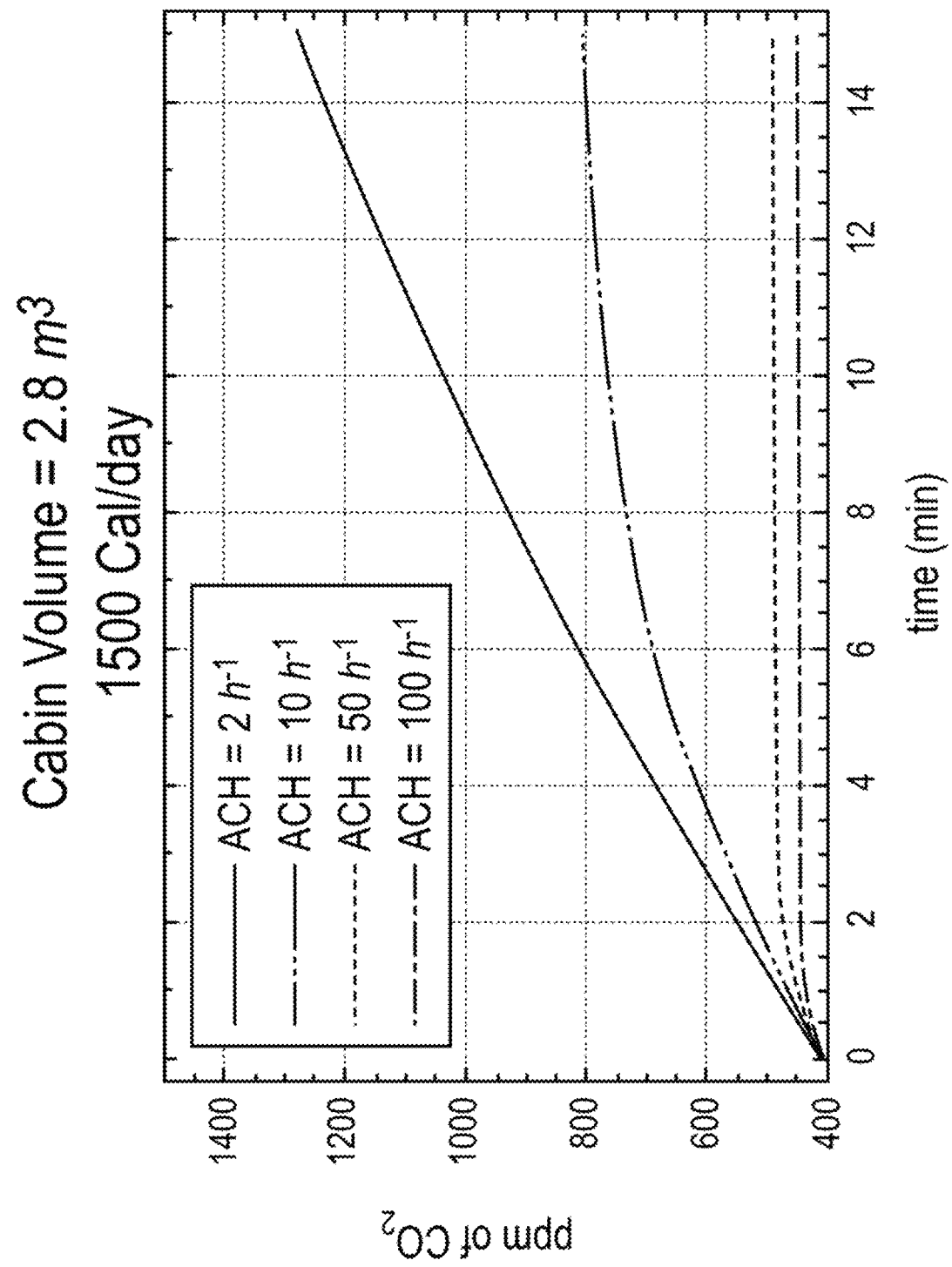
FIG. 6 demonstrates an exemplary graph of indirect calorimetry as a predetermined daily caloric intake for different air exchange rates, in accordance with some embodiments of the disclosure provided herein.
Figure 7:
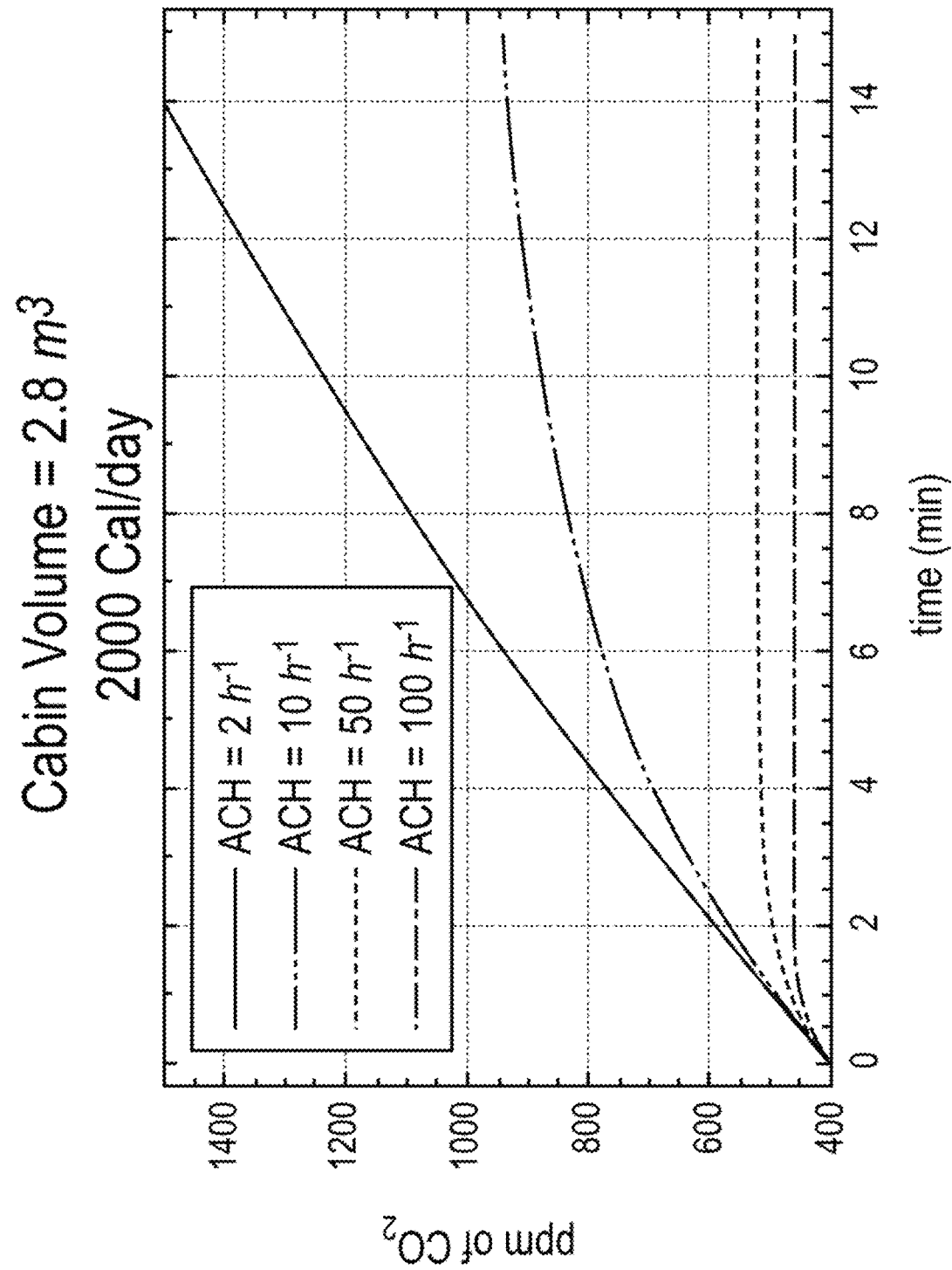
FIG. 7 demonstrates an exemplary graph of indirect calorimetry as a predetermined daily caloric intake for different air exchange rates, in accordance with some embodiments of the disclosure provided herein.

FIG. 3 demonstrates an exemplary graph of indirect calorimetry as a function of glucose and gas volume, in accordance with some embodiments of the disclosure provided herein.

In the present embodiment, ASHRAE assumes 30,000 ppm/h for two quiet seated adults, which is consistent with the plot above since typical adult has basal metabolic rate of ~1800 Cal/day. ASHRAE is the American Society of Heating, Refrigerating and Air Conditioning Engineers who with American National Standards Institute (ANSI) promulgate standards relating present and related arts.

Thus, the enclosed space like car cabin provides direct measure of the instantaneous metabolic rate of a single driver by directly measuring $CO_2$ generation rate.

The tables of TEE are available for humans based on gender, age, and weight as well as for various animals other than humans. In general, mass of the animal (including human) and TEE are related by allometric scaling relations and thus measurement of mass alone provides pretty good estimate of the $CO_2$ generation.

The Air Exchange Rate (AER) for the vehicles depends on the speed, age, and type of the car as well as ventilation settings such as fan speed, recirculation (RC) or outside air intake (OA). For a parked car, AER~2-5 $h^{-1}$. For a moving car, it depends on the speed and AER ranges from 20-200 $h^{-1}$. Much of this is documented at length by the researchers in the transportation industry.

FIGS. 4-7 demonstrates an exemplary graph of indirect calorimetry as a predetermined daily caloric intake for different air exchange rates, in accordance with some embodiments of the disclosure provided herein. The plot of $CO_2$ concentration in the car for different Air Exchange Rate (AER) is shown in FIGS. 4-7.

For a typical moving vehicle on the road, AER~30-200 $h^{-1}$, can be estimated by the vehicle manufacturer from the state of the ventilation system, vehicle speed, position of windows, as well as the age of the vehicle. Since the equilibrium value of the $CO_2$ depends only on the Air Exchange Rate (AER) and the cabin volume:

$$c_{eq} = n_{people} \frac{S_{co_2}}{AERV_0} \qquad (4)$$

Thus, the number of people can be determined from Equation 4 and measurement of $c_{eq}$.

On the other hand, if one knows the number of people, then equilibrium concentration can be used to estimate the Air Exchange Rate (AER) and hence the load on the heating and the cooling system. Thus, Air Exchange Rate (AER) can be modulated automatically to keep the internal pollutants at low level and air healthy. This is particularly important if the outside air has high PM level. The Air Exchange Rate (AER) in such a case has to be lowered (by using RC) to improve filtering efficiency but not so low so as to increase the internal pollution levels.

Figure 8:
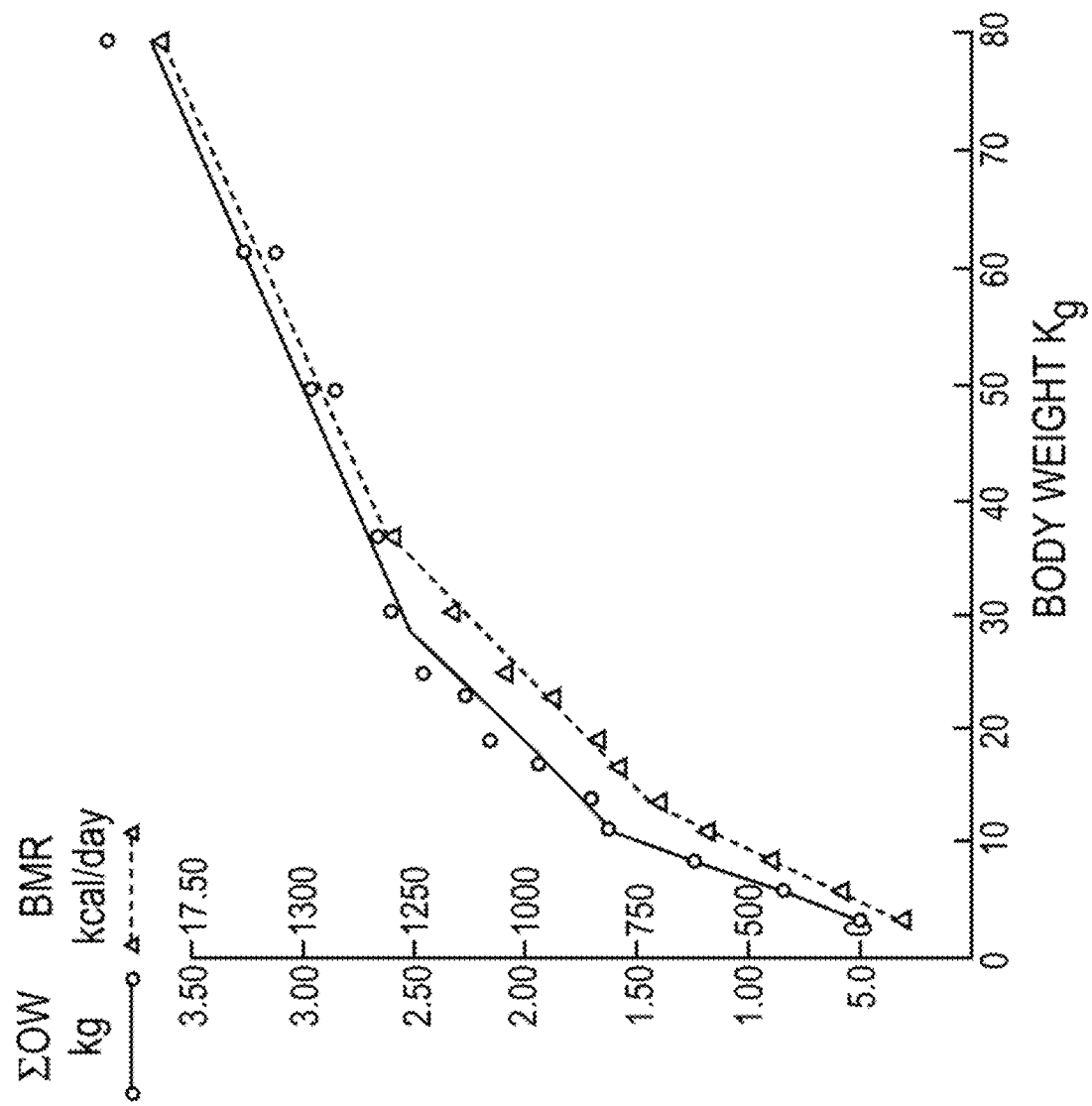
FIG. 8 demonstrates an exemplary graph of Basal metabolic rates for infants, in accordance with some embodiments of the disclosure provided herein.

FIG. 8 demonstrates an exemplary graph of Basal metabolic rates for infants, in accordance with some embodiments of the disclosure provided herein. Basal metabolic rate (BMR) is the rate of energy expenditure per unit time by endothermic animals at rest. It is reported in energy units per unit time ranging from watt (joule/second) to ml 02/min or joule per hour per kg body mass J/(h·kg).

Proper measurement requires a strict set of criteria be met. These criteria include being in a physically and psychologically undisturbed state, in a thermally neutral environment, while in the post-absorptive state (i.e., not actively digesting food). In bradymetabolic animals, such as fish and reptiles, the equivalent term standard metabolic rate (SMR) is used. It follows the same criteria as BMR, but requires the documentation of the temperature at which the metabolic rate was measured. This makes BMR a variant of standard metabolic rate measurement that excludes the temperature data, a practice that has led to problems in defining "standard" rates of metabolism for many mammals.

The BMR of small children and infants is shown in FIG. 8. The data shows that newborns may have a TEE of ~250-300 Cal/d which rises rapidly as infants gain weight.

Figure 9:
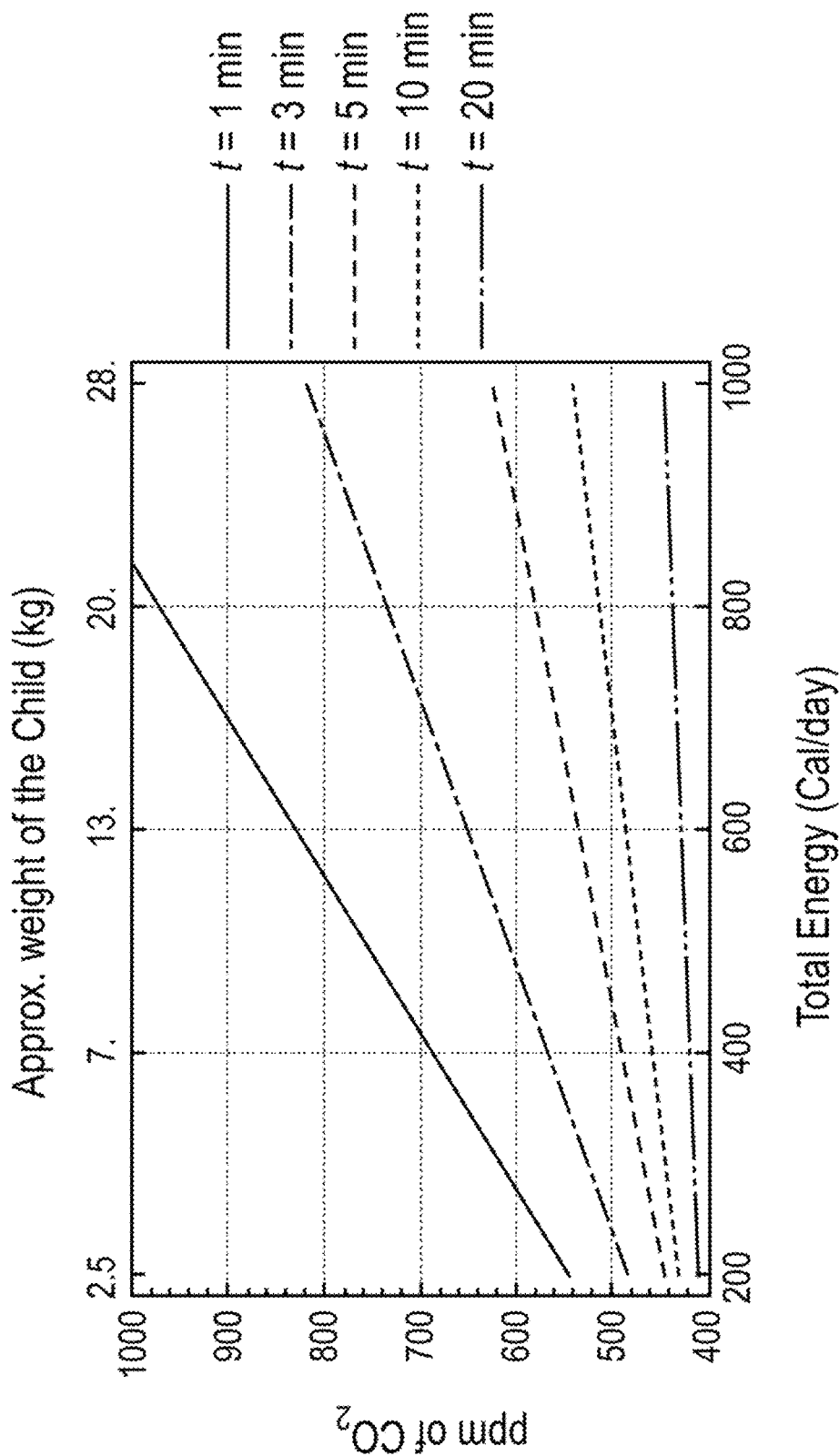
FIG. 9 demonstrates an exemplary graph showing a rise in $CO_2$ concentration for different metabolic rates, in accordance with some embodiments of the disclosure provided herein.

FIG. 9 demonstrates an exemplary graph showing a rise in $CO_2$ concentration for different metabolic rates, in accordance with some embodiments of the disclosure provided herein. From the above plots, we may easily be able to deduce the presence of a small child in a parked car by measuring $CO_2$ every few mins. This can be accomplished by intermittently running the ventilation fan in recirculation mode. The AER may be as low as 2 $h^{-1}$ in such conditions. In the plot of FIG. 9, we show the rise in $CO_2$ concentration for different metabolic rates.

One can simultaneously measure the increase in the cabin temperature of the parked car to determine whether stress is increasing on the child or a pet left in the car. An alarm or automatic emergency call may be made by the automobile to alert the emergency services or parent once a predetermined temperature threshold is reached in conjunction with rising $CO_2$.

Figure 10:
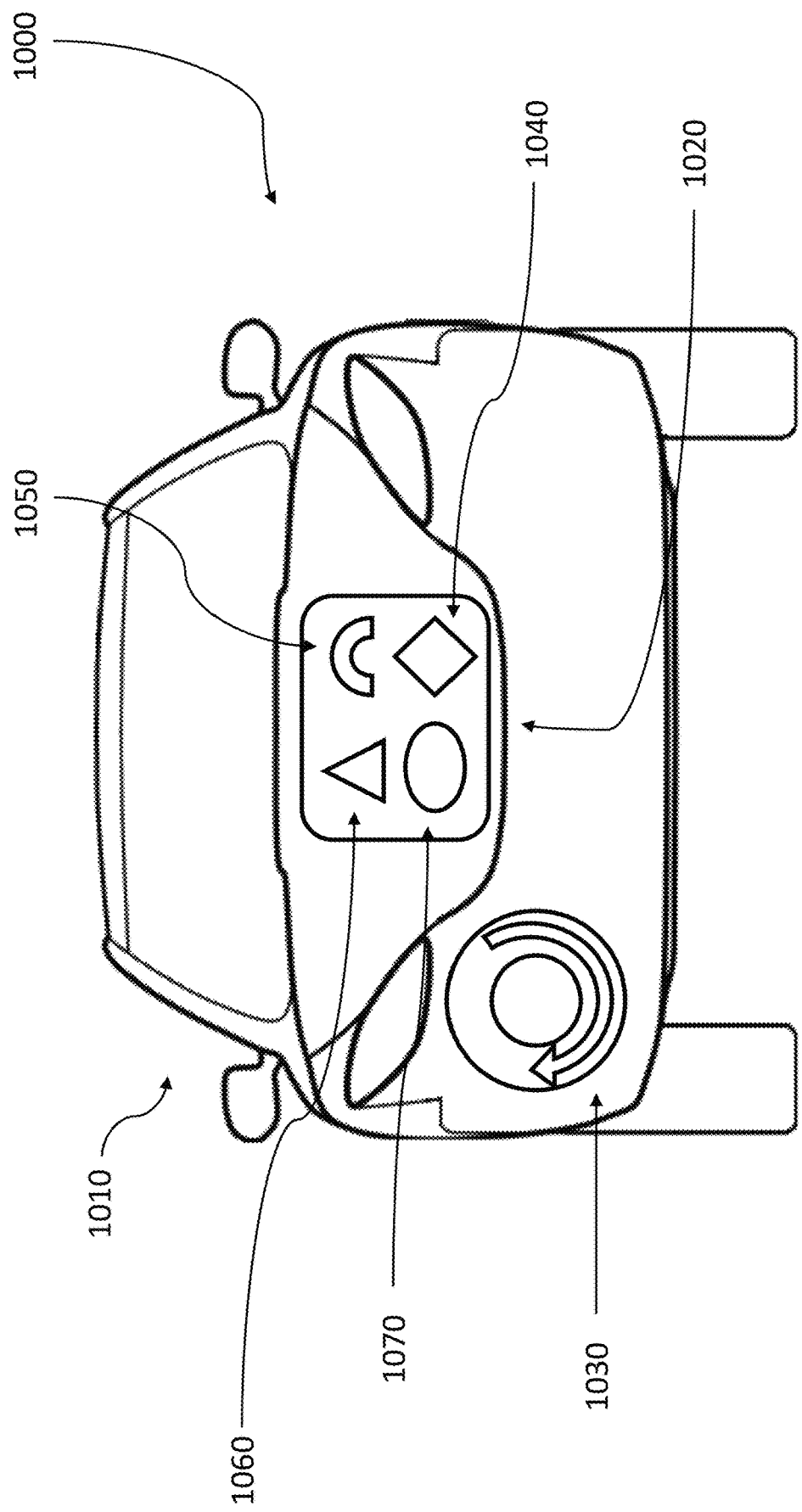
FIG. 10 shows an exemplary front view of an automobile sensory system, in accordance with one or more embodiments of the disclosure provided herein.

FIG. 10 shows an exemplary front view of an automobile sensory system, in accordance with one or more embodiments of the disclosure provided herein. Automobile sensor system 1000 comprises car 1010, recirculatory system 1030 and sensor suite 1020. Sensor suite 1020 comprises one or more of gas sensors 1040, particulate matter sensor 1060, temperature sensor 1050, and GPS device 1070.

As can be appreciated by one skilled in the art, recirculatory system 1030 comprises an inlet from the ambient environment, an electromechanical fan, vent blocker, damper, jumper, deflector and/or some other means for gas redirection. Pursuant to the previous embodiments, recirculatory system 1030 performs to let in fresh outside air, shut it off completely, or some combination therebetween.

While the present disclosure primarily focuses on automobiles, other vehicles are not beyond the scope of the invention. For example, construction and farming vehicles (backhoe, combines, etc.) are entirely applicable. Particularly because there is usually more particulate matter present, there is a greater need for use in these. Airplanes, busses, jets, trains and other public transportation are all within the scope of the present invention. Other closed environments would also have a need, e.g., underground bunkers, safe rooms, and even crane operators.

Select Examples

Example 1 provides a vehicle sensor system configured to detect the presence of the living human or pet based upon its metabolic rate in a vehicle, the system comprises a carbon dioxide sensor, a temperature sensor, a ventilation controller, non-volatile memory, and a processor configured to sample the ambient air inside an automobile, determine the presence of a living animal based at least on information from the temperature sensor and carbon dioxide sensor, and send control information to the ventilation controller.

Example 2 provides a vehicle sensor system configured to detect the presence of the living human or pet based upon its metabolic rate in a vehicle according to example 1, wherein the control information includes a shutoff command which is configured to close off outside air from entering into a cabin of the vehicle.

Example 3 provides a vehicle sensor system configured to detect the presence of the living human or pet based upon its metabolic rate in a vehicle according to example 2, wherein the control information includes a full-open command which is configured to maximize the flow of outside air into the cabin.

Example 4 provides a vehicle sensor system configured to detect the presence of the living human or pet based upon its metabolic rate in a vehicle according to example 1 further comprising a particulate matter sensor.

Example 5 provides a vehicle sensor system configured to detect the presence of the living human or pet based upon its metabolic rate in a vehicle according to example 1 further comprising a gas sensor.

Example 6 provides a vehicle sensor system configured to detect the presence of the living human or pet based upon its metabolic rate in a vehicle according to example 1 further comprising GPS receiver.

Example 7 provides a vehicle sensor system configured to detect the presence of the living human or pet based upon its metabolic rate in a vehicle according to example 1 further comprising a humidity sensor.

Example 8 provides a vehicle sensor system configured to detect the presence of the living human or pet based upon its metabolic rate in a vehicle according to example 1, wherein the non-volatile memory includes a look-up table.

Example 9 provides a vehicle sensor system configured to detect the presence of the living human or pet based upon its metabolic rate in a vehicle according to example 1, wherein the processor is configured to send information relating to a distress call.

Example 10 provides a vehicle sensor system configured to detect the presence of the living human or pet based upon its metabolic rate in a vehicle according to example 1, wherein the processor is configured to calculate the number of occupants in the vehicle.

Example 11 provides a vehicle sensor system configured to detect the presence of the living human or pet based upon its metabolic rate in a vehicle according to example 10, further comprising at least one weight sensor configured to measure the weight of an occupant of the vehicle.

Example 12 provides a vehicle sensor system configured to detect the presence of the living human or pet based upon its metabolic rate in a vehicle according to example 11, wherein the processor is further configured to further refine the occupancy determination based upon the weight information from the seat to improve the estimate of the type and number of people in the car.

Example 13 provides a vehicle sensor system configured to detect the presence of the living human or pet based upon its metabolic rate in a vehicle according to example 12, wherein the processor is further configured to further refine the occupancy determination by changing the AER of the car by modulating the ventilation controller.

Example 14 provides a vehicle sensor system configured to detect the presence of the living human or pet based upon its metabolic rate in a vehicle according to example 4, wherein the ventilation controller is configured to optimize air quality based on at least information from the particulate and carbon dioxide sensors.

Example 15 provides a method to detect the presence of the living human or pet and based upon its metabolic rate in a vehicle, the method comprises sensing carbon dioxide, measuring a temperature, controlling a ventilation system, sampling the ambient air inside an automobile, determining the presence of a living animal based at least on information from the temperature and carbon dioxide, and sending control information to change the ventilation system.

Example 16 provides the method to detect the presence of the living human or pet and based upon its metabolic rate in a vehicle, according to example 15, wherein the control information includes a shutoff command which is configured to close off outside air from entering into a cabin of the vehicle.

Example 17 provides the method to detect the presence of the living human or pet and based upon its metabolic rate in a vehicle, according to example 16, wherein the control information includes a full-open command which is configured to maximize the flow of outside air into the cabin.

Example 18 provides the method to detect the presence of the living human or pet and based upon its metabolic rate in a vehicle, according to example 15, further comprising sensing particulate matter.

Example 19 provides the method to detect the presence of the living human or pet and based upon its metabolic rate in a vehicle, according to example 15, further comprising sensing a predetermined gas.

Example 20 provides the method to detect the presence of the living human or pet and based upon its metabolic rate in a vehicle, according to example 15 further comprising determining position based on GPS.

Example 21 provides the method to detect the presence of the living human or pet and based upon its metabolic rate in a vehicle, according to example 15 further comprising sensing humidity.

Example 22 provides the method to detect the presence of the living human or pet and based upon its metabolic rate in a vehicle, according to example 15 further comprising calculating a number of occupants in the vehicle.

Example 23 provides the method to detect the presence of the living human or pet and based upon its metabolic rate in a vehicle, according to example 22 further comprising sensing the weight of an occupant of the vehicle.

Example 24 provides an apparatus to detect the presence of the living human or pet and based upon its metabolic rate in a vehicle comprising means for sensing carbon dioxide, means for measuring a temperature, means for controlling a ventilation system, means for sampling the ambient air inside an automobile, means for determining the presence of a living animal based at least on information from the temperature and carbon dioxide, and means for sending control information to change the ventilation system.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Note that the activities discussed above with reference to the FIGURES which are applicable to any integrated circuit that involves signal processing (for example, gesture signal processing, video signal processing, audio signal processing, analog-to-digital conversion, digital-to-analog conversion), particularly those that can execute specialized software programs or algorithms, some of which may be associated with processing digitized real-time data.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe.

Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smart phone, a mobile phone, an iPad, or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

In some embodiments, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc.

Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure.

In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Interpretation of Terms

All definitions, as defined and used herein, should be understood to control over dictionary definitions, definitions in documents incorporated by reference, and/or ordinary meanings of the defined terms. Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A vehicle sensor system, comprising:
   a carbon dioxide sensor placed in a ventilation system of a vehicle and configured to measure carbon dioxide inside a cabin of the vehicle;
   a temperature sensor configured to measure a temperature inside the cabin of the vehicle;
   a ventilation controller configured to optimize air quality inside the cabin of the vehicle;
   non-volatile memory; and
   a processor communicatively coupled to the non-volatile memory and configured to:
      measure the carbon dioxide inside the cabin of the vehicle by periodically sampling ambient air inside the cabin through intermittent operation of the ventilation system in a defined mode of operation;
      measure a metabolic rate associated with a number of vehicle occupants based on the measured carbon dioxide inside the cabin of the vehicle;
      determine an air exchange rate (AER) corresponding to a concentration of fresh air being exchanged in the vehicle;
      determine the number of vehicle occupants based on weight information from seat weight sensors, the temperature inside the cabin from the temperature sensor, the carbon dioxide inside the cabin from the carbon dioxide sensor, and the AER of the vehicle; and
      send control information based on at least the number of vehicle occupants and the metabolic rate to adjust operation of the ventilation controller to optimize the air quality inside the cabin of the vehicle.

2. The vehicle sensor system according to claim 1, wherein the control information includes a shutoff command which is configured to close off outside air from entering into the cabin of the vehicle.

3. The vehicle sensor system according to claim 1, wherein the control information includes a full-open command which is configured to fully open a flow of outside air into the cabin.

4. The vehicle sensor system according to claim 1, further comprising a particulate matter sensor.

5. The vehicle sensor system according to claim 1, further comprising a gas sensor.

6. The vehicle sensor system according to claim 1, further comprising a GPS receiver.

7. The vehicle sensor system according to claim 1, further comprising a humidity sensor.

8. The vehicle sensor system according to claim 1, wherein the non-volatile memory includes a look-up table.

9. The vehicle sensor system according to claim 8, wherein the processor is further configured to send information relating to a distress call.

10. The vehicle sensor system according to claim 1, wherein the processor is further configured to determine the number of vehicle occupants based on changing the AER of the vehicle by modulating the ventilation controller.

11. The vehicle sensor system according to claim 1, wherein the defined mode of operation is a recirculation mode.

12. The vehicle sensor system according to claim 4, wherein the ventilation controller is configured to optimize the air quality based on at least information from the particulate matter sensor and the carbon dioxide sensor.

13. A method, comprising:
sensing a concentration of carbon dioxide inside a cabin of a vehicle;
measuring a temperature inside the cabin of the vehicle;
controlling a ventilation system;
measuring the carbon dioxide inside the cabin of the vehicle by periodically sampling ambient air inside the cabin through intermittent operation of the ventilation system in a defined mode of operation;
measuring a metabolic rate associated with a number of vehicle occupants based on the measured carbon dioxide inside the cabin of the vehicle;
determining an air exchange rate (AER) corresponding to a concentration of fresh air being exchanged in the vehicle;
determining the number of vehicle occupants based on weight information from seat weight sensors, the temperature and the concentration of the carbon dioxide inside the cabin, and the AER of the vehicle; and
sending control information based on at least the number of vehicle occupants and the metabolic rate to change operation of the ventilation system to optimize the air quality inside the cabin of the vehicle.

14. The method according to claim 13, wherein the control information includes a shutoff command which is configured to close off outside air from entering into the cabin of the vehicle.

15. The method according to claim 14, wherein the control information includes a full-open command which is configured to fully open a flow of the outside air into the cabin.

16. The method according to claim 13, further comprising:
determining that the temperature has exceeded a predetermined threshold temperature; and
sending a distress call.

17. An apparatus, comprising:
means for sensing a concentration of carbon dioxide inside a cabin of a vehicle;
means for measuring a temperature inside the cabin of the vehicle;
means for controlling a ventilation system;
means for measuring the carbon dioxide inside the cabin of the vehicle by periodically sampling ambient air inside the cabin through intermittent operation of the ventilation system in a defined mode of operation;
means for measuring a metabolic rate associated with a number of vehicle occupants based on the measured carbon dioxide inside the cabin of the vehicle;
means for determining an air exchange rate (AER) corresponding to a concentration of fresh air being exchanged in the vehicle;
means for determining the number of vehicle occupants based on weight information from seat weight sensors, the temperature and the concentration of the carbon dioxide inside the cabin, and the AER of the vehicle; and
means for sending control information based on at least the number of vehicle occupants and the metabolic rate to change operation of the ventilation system to optimize the air quality inside the cabin of the vehicle.

* * * * *